US010023902B2

(12) United States Patent
Parker et al.

(10) Patent No.: US 10,023,902 B2
(45) Date of Patent: Jul. 17, 2018

(54) METHODS FOR DETECTING ENZYME ACTIVITY USING FLUORESCENCE LIFETIME IMAGING

(71) Applicant: Purdue Research Foundation, West Lafayette, IN (US)

(72) Inventors: Laurie Louise Parker, Minneapolis, MN (US); Joseph Maria Kumar Irudayaraj, West Lafayette, IN (US); Andrew M. Lipchik, Palo Alto, CA (US); Nur Pradani Damayanti, West Lafayette, IN (US)

(*) Notice: Subject to any disclaimer, the term of this patent is extended or adjusted under 35 U.S.C. 154(b) by 418 days.

(21) Appl. No.: 14/027,107

(22) Filed: Sep. 13, 2013

(65) Prior Publication Data
US 2014/0072516 A1 Mar. 13, 2014

Related U.S. Application Data

(60) Provisional application No. 61/700,878, filed on Sep. 13, 2012, provisional application No. 61/766,067, filed on Feb. 18, 2013.

(51) Int. Cl.
*C12Q 1/48* (2006.01)
*A61K 49/00* (2006.01)
*C12Q 1/50* (2006.01)

(52) U.S. Cl.
CPC .......... *C12Q 1/485* (2013.01); *A61K 49/0056* (2013.01); *C12Q 1/50* (2013.01)

(58) Field of Classification Search
None
See application file for complete search history.

(56) References Cited

U.S. PATENT DOCUMENTS

| 2005/0054573 | A1* | 3/2005 | Werner | C07K 7/06 435/194 |
| 2005/0064481 | A1* | 3/2005 | Korfhage | C12Q 1/6813 435/6.11 |
| 2010/0304407 | A1* | 12/2010 | Gray | C12Q 1/42 435/7.72 |
| 2011/0046018 | A1 | 2/2011 | Chen et al. | |

OTHER PUBLICATIONS

Wouters et al (1999 Current Biology 9:1127-30).*
Akiba, et al., Selective Detection of Phosphotyrosine in the Presence of Various Phosphate-Containing Biomolecules with the Aid of a Terbium (III) Complex, ChemBioChem, 2009, vol. 10, p. 1773-1776.
Akiba, et al., Binuclear Terbium (III) Complex as a Probe for Tyrosine Phosphorylation, Chem. Eur. J., 2010, vol. 16, p. 5018-5025.
Amanchy, et al., Identification of Novel Phosphorylation Motifs Through an Integrative Computational and Experimental Analysis of the Human Phosphoproteome, J Proteomics Bioinform, vol. 4, Iss. 2, p. 022-035.
Atkinson, et al., A Cationic Lanthanide Complex Binds Selectively to Phosphorylated Tyrosine Sites, Aiding NMR Analysis of the Phosphorylated Insulin Receptor Peptide Fragment, Org. Biomol. Chem., 2006, vol. 4, p. 3166-317.
Balakrishnan, et al., Design of a Protein Kinase-Inducible Domain, J. Am. Chem. Soc., 2006, vol. 128, p. 5590-5591.
Chen, et al., Discovery of Protein Phosphorylation Motifs through Exploratory Data Analysis, PLos One, vol. 6, Iss. 5, p. 1-15.
Dang, et al., Prediction of Kinase-Specific Phosphorylation Sites Using Conditional Random Fields, Bioinformatics, 2008, vol. 24, Iss. 24, p. 2857-2864.
He, et al., Motif-All: Discovering All Phosphorylation Motifs, BMC Bioinformatics, 2011, vol. 12, Iss. 1, p. 1-8.
Horton, et al., Multiplexing Terbium- and Europium-Based TR-FRET Readouts to Increase Kinase Assay Capacity, Journal of Biomolecular Screening, 2010, vol. 15, Iss. 8, p. 1008-1015.
Jung, et al., PostMod: Sequence Based Prediction of Kinase-Specific Phosphorylation Sites with Indirect Relationship, BMC Bioinformatics, 2010, vol. 11, Iss. 1, p. 1-10.
Li, et al., Prediction of Kinase-Specific Phosphorylation Sites with Sequence Features by a Long-Odds Ratio Approach, Proteins, 2008, vol. 70, p. 404-414.
Linding, et al., NetworKIN: A Resource for Exploring Cellular Phosphorylation Networks, Nucleic Acids Research, 2008, vol. 36, p. D695-D699.
Liu, et al., Phosphorylation-Dependent Metal Binding by $\alpha$-Synuclein Peptide Fragments, J. Biol. Chem., 2007, vol. 12, p. 234-247.
Liu, et al., Phosphorylation of an $\alpha$-Synuclein Peptide Fragment Enhances Metal Binding, J. Am. Chem. Soc., 2005, vol. 127, p. 9662-9663.
Miller, et al., Linear Motif Atlas for Phosphorylation-Dependent Signaling, Science Signaling, 2008, vol. 1, Iss. 35, p. 1-11.
Neuberger, et al., pkaPS: Prediction of Protein Kinase a Phosphorylation Sites with the Simplified Kinase-Substrate Binding Model, Biology Direct, 2007, vol. 2, Iss. 1, p. 1-23.
Nitz, et al., A Powerful Combinatorial Screen to Identify High-Affinity Terbium (III)—Binding Peptides, Chem. Bio. Chem., 2003, vol. 4, p. 272-276.
Obenauer, et al., Scansite 2.0: Proteome-Wide Prediction of Cell Signaling Interactions Using Short Sequence Motifs, Nucleic Acids Research, 2003, vol. 31, Iss. 13, p. 3635-3641.
Pazos, et al., Detection of Phosphorylation States by Intermolecular Sensitization of Lanthanide-Peptide Conjugates, Chem. Commun., 2012, vol. 48, p. 9534-9536.
Saunders, et al., Predikin and PredikinDB: A Computational Framework for the Prediction of Protein Kinase Peptide Specificity and an Associated Database of Phosphorylation Sites, BMC Bioinformatics, 2008, vol. 9, p. 1-11.
Saunders, et al., The Predikin Webserver: Improved Prediction of Protein Kinase Peptide Specific Using Structural Information, Nucleic Acids Research, 2008, vol. 36, p. W286-W290.
Sculimbrene, et al., Lanthanide-Binding Tags as Luminescent Probes for Studying Protein Interactions, J. Am. Chem. Soc., 2006, vol. 128, p. 7346-7352.

(Continued)

*Primary Examiner* — Christopher M Gross
(74) *Attorney, Agent, or Firm* — D'Hue Law LLC; Cedric A. D'Hue

(57) ABSTRACT

Disclosed are methods of detecting enzymatic activity on a fluorophore-labeled substrate using by monitoring the fluorescence lifetime of the fluorophore.

15 Claims, 11 Drawing Sheets

(56) References Cited

OTHER PUBLICATIONS

Sobolev, et al., Functional Classification of Proteins Based on Projection of Amino Acid Sequences: Application for Prediction of Protein Kinase Substrates, BMC Bioinformatics, 2010, vol. 11, p. 1-18.
Tremblay, et al., A Luminescent Sensor for Tyrosine Phosphorylation, Organic Letters, 2008, vol. 10, No. 1, p. 5-8.
Tremblay, et al., Phosphorylation State-Responsive Lanthanide Peptide Conjugates: A Luminescence Switch Based on Reversible Complex Reorganization, Organic Letters, 2006, vol. 8, Iss. 13, p. 2723-2726.
Xue, et al., GPS: A Comprehensive www Server for Phosphorylation Sites Prediction, Nucleic Acids Research, 2005, vol. 33, p. W184-W187.
Xue, et al., GPS 2.0, a Tool to Predict Kinase-Specific Phosphorylation Sites in Hierarchy, Molecular & Cellular Proteomics 7.9, 2008. p. 1598-1608.
Wong, et al., KinasePhos 2.0: A Web Server for Identifying Protein Kinase-Specific Phosphorylation Sites Based on Sequences and Coupling Patterns, Nucleic Acids Research, 2007, vol. 35, p. W588-W594.
Zondlo, et al., Design of an Encodable Tyrosine Kinase-Inducible Domain: Detection of Tyrosine Kinase Activity by Terbium Luminescence, J. Am. Chem. Soc., 2010, vol. 132, p. 5619-5621.

\* cited by examiner

METHODS FOR DETECTING ENZYME ACTIVITY USING FLUORESCENCE LIFETIME IMAGING

CROSS-REFERENCE TO RELATED APPLICATIONS

This application claims the benefit of priority to U.S. Provisional Application No. 61/700,878 filed Sep. 13, 2012, and U.S. Provisional Application No. 61/766,067 filed Feb. 18, 2013, each of which is incorporated by reference in its entirety.

STATEMENT REGARDING FEDERALLY SPONSORED RESEARCH AND DEVELOPMENT

This invention was made with government support under CA127161 awarded by the National Institutes of Health. The government has certain rights in the invention.

INTRODUCTION

Currently it is very difficult to measure the activities of enzymes in living cells in real time. Because of this, the heterogeneity between cells and subcellular details of enzymatic signaling are poorly understood. These subcellular details are critical to understanding drug sensitivity and resistance mechanisms in many diseases, in particular, localization of enzyme signaling and cell-to-cell heterogeneity are major factors in determining the success of cancer treatments and the likelihood of recurrence.

Many cancers exhibit deregulated activity of protein kinase enzymes. Kinase inhibitors have been used to treat cancer, but not all cancers are sensitive to inhibitor drugs. Phosphorylation dynamics in complex tissues are not well understood. Live, subcellular analysis can reveal the details of kinase signaling in mixed populations of cells. However, measuring subcellular kinase activity in living cells remains a major challenge.

Commonly, methods used to detect intracellular post-translational modifications such as phosphorylation require lysis of cells to detect substrate modification. Lysis interferes with assessment of enzyme activity and subcellular localization. Others have used genetically-engineered expressed proteins to detect enzyme activities in intact, living cells. This is commonly performed using Forster resonance energy transfer (FRET) between at least two fluorophores or a fluorophore and a quencher, which is stimulated by the binding of a modified portion of the protein with a recognition domain in such a way as to bring the two fluorophores within the required Forster radius for energy transfer. These methods are generally coupled with fluorophore intensity-based readouts. Some of these strategies use fluorescence lifetime detection, by measuring the decrease in lifetime of the fluorophore that is acting as a FRET donor. However, these methods are limited by challenges. It is difficult to obtain uniform transfection and expression of protein fluorophores, particularly in primary patient-derived cells or tissues. Additionally, the large protein fluorescent labels can affect substrate function and interaction with a kinase. Further, FRET is limited by its low signal to noise ratio. Intensity-based fluorescence is confounded by photobleaching when experiments are conducted over long time periods, which makes it difficult to interpret subcellular fluctuations at high spatial and temporal resolution.

There is a need in the art for methods for detecting enzymatic activity within a cell, including enzyme-catalyzed posttranslational modifications (PTMs) in general, and kinase activity in particular. The present invention addresses these needs.

SUMMARY

In one embodiment, the present invention provides methods for detecting the activity of an enzyme that catalyzes a PTM to a substrate. In certain embodiments, the method includes contacting an intact cell with a biosensor comprising a fluorophore-tagged polypeptide, peptidomimetic, or nucleic acid mimetic that can serve as a substrate for the enzyme of interest. The enzyme catalyzes a modification of the biosensor in a manner similar to its native activity, e.g., an enzyme that natively catalyzes the phosphorylation of a tyrosine residue in a protein substrate catalyzes the phosphorylation of a tyrosine residue in a biosensor that includes a polypeptide substrate sequence. The fluorescence lifetime is monitored over time using fluorescence lifetime spectroscopy and/or fluorescence lifetime imaging microscopy (FLIM). A change in fluorescence lifetime of the biosensor is indicative of a modification to the biosensor and is correlated with enzyme activity of the environment.

In certain embodiments, the substrate of the biosensor is designed based on information about known substrates for the enzyme of interest. Any suitable method of designing enzyme substrate may be used, including, for example, methods described in U.S. patent application Ser. No. 13/761,968, filed Feb. 7, 2013, which is incorporated by reference in its entirety.

In certain embodiments, the methods involve detecting the activity of a kinase. In certain embodiments, the kinase is a serine/threonine kinase. In certain embodiments, the kinase is a threonine kinase. In certain embodiments, the threonine kinase is Syk, Btk, a Src family threonine kinase, Jak2, or an Abl family tyrosine kinase.

In certain embodiments, the methods involve detecting the activity of an enzyme that catalyzes a PTM other than phosphorylation, which may include, without limitation, hydroxylation, acylation, alkylation, adenylylation, glycosylation, lipidation, and ubiquitylation. In certain embodiments, the PTM is a lipidation selected from myristoylation, palmitoylation, isoprenylation, and prenylation.

In certain embodiments, the biosensor comprises a synthetic polypeptide. The synthetic polypeptide may be synthesized chemically or, alternatively, synthesized in vivo, for example, in a transgenic bacterium expressing the polypeptide, and subsequently purified.

In certain embodiments, the biosensor comprises a peptidomimetic. In certain embodiments, the peptidomimetic comprises one or more D-amino acids, one or more modified amino acids, a modified backbone, e.g., a substitution of one or more peptide bonds with a non-hydrolyzable bond, and/or a retro, inverso, or retro-inverso sequence of a polypeptide substrate sequence.

The synthetic peptide or peptidomimetic of the biosensor is labeled with a suitable fluorophore. In certain embodiments, the fluorophore is an organic fluorophore. In certain embodiments, the organic fluorophore is a small molecule, i.e., a molecule with a molecular weight of about 1200 Da or less. Any fluorophore that is susceptible to fluorescence lifetime shifts in the environment in which a posttranslational modification occurs is suitable for use in the methods of the invention. Properties of a molecule that are responsible for fluorescence, e.g. extended conjugation systems, and delocalized electrons in amino and oxygen-containing groups, are also likely to confer lifetime shift susceptibility. Examples of suitable fluorophore labels include, without limitation: the Cy series of dyes, including, for example, Cy3, Cy5, Cy5.5, Cy7, and Cy7.5; the AlexaFluor series of dyes, including, for example, AlexaFluor488, AlexaFluor647, and AlexaFluor555; the DyLight series of dyes, including, for example, DyLight488 and DyLight555; fluorescein and derivatives; rhodamine and derivatives; coumarin and derivatives; nitrobenzoxadiazole and derivative; BODIPY and derivatives; pyrene and derivatives; dansyl and derivatives; pthalimides and derivatives; and/or protein fluorophores, such as EGFP, RFP, CFP, and YFP.

In certain embodiments, the fluorophore is covalently attached to the substrate. The distance between the fluorophore and the site of the PTM depends on the shape of the binding pocket. Suitable distances for placement of the fluorophore may be determined using information about the binding pocket of the enzyme of interest, including, for example, crystal structures, or predicted folded structures, or through routine experimentation. In certain embodiments, the fluorophore may be placed from one to eight amino acids away from the site of the PTM, or from three to six amino acids from the PTM site; however, in other embodiments, the fluorophore may be placed further away from the site of PTM.

In certain embodiments, the biosensor may include a moiety to enhance delivery into the cell. In certain embodiments, the moiety is a cell penetrating peptide, for example, a TAT peptide, that is linked to the synthetic peptide or peptidomimetic.

In certain embodiments, the biosensor is delivered into the cell using a vehicle to enhance cellular uptake, which may include, for example, a liposome. In certain embodiments, the biosensor or the biosensor and its vehicle are provided in a pharmaceutically acceptable excipient.

In certain embodiments, the biosensor is delivered directly to the cell ex vivo or in vitro. In other embodiments, the biosensor is used to detect intracellular enzyme activity in vivo, following administration of the biosensor to an organism comprising the cell. Any suitable mode of administration of the biosensor may be used, including, without limitation, oral or parenteral administration of the biosensor or a vehicle containing the biosensor. In certain embodiments, the biosensor or its delivery vehicle may include a targeting moiety to target the biosensor to particular cell types. Targeting moieties may include, for example, an antibody directed to an epitope specific to a certain cell type or a ligand that binds to a particular receptor.

Following delivery of the biosensor to the cell, fluorescence of the cell is monitored over time. Information about the fluorescence lifetime of the fluorophore is used to determine whether the biosensor has been modified, which modification is related to activity of the enzyme in the cell. In certain embodiments, the information may be used to determine subcellular localization of the enzyme in the cell.

In certain embodiments, the invention includes a system for detecting posttranslational modification activity of an enzyme using a biosensor comprising a fluorophore-tagged polypeptide, peptidomimetic, or nucleic acid mimetic that can serve as a substrate for the enzyme of interest. The enzyme catalyzes a modification of the biosensor in a manner similar to its native activity. The fluorescence lifetime is monitored over time using fluorescence lifetime spectroscopy and/or fluorescence lifetime imaging microscopy (FLIM). The fluorescence lifetime is of the biosensor is analyzed to determine whether there has been a change in fluorescence lifetime indicative of a modification to the biosensor and is correlated with enzyme activity.

DETAILED DESCRIPTION

Figure 1:
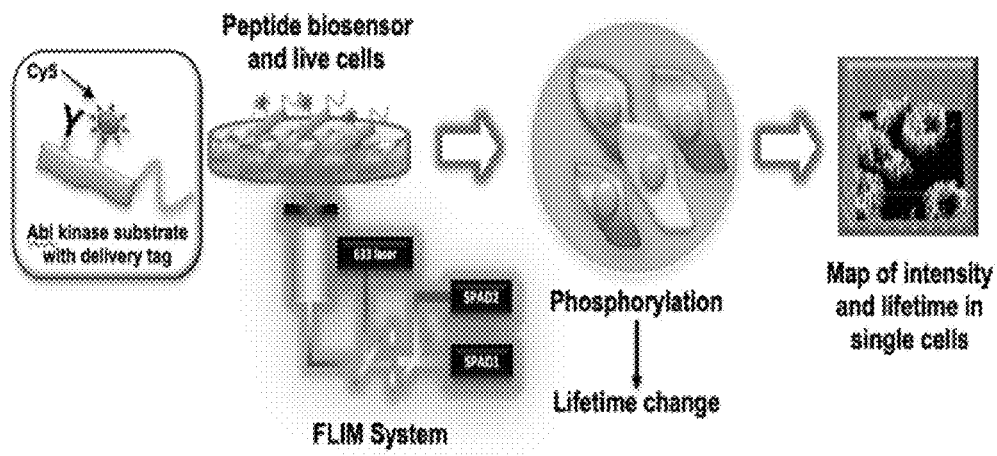
FIG. 1 depicts the use of FLIM to detect phosphorylation-dependent lifetime shifts for biosensors in live, intact cells.

The methods described herein are directed to methods of detecting enzymatic modifications of a biosensor comprising a peptide or peptidomimetic substrate of an enzyme using changes to the lifetime of a fluorophore attached to the peptide. The changes to the fluorophore lifetime occur because of recognition and binding of the modified peptide product by other biomolecules, e.g. protein-protein interaction domains, which are present in proximity to the modified peptide. Upon binding of the fluorophore-labeled modified peptide to the protein, the local physiochemical environment of the fluorophore is altered in such a way as to stabilize the lifetime, resulting in an increased lifetime. Examples of changes in the physiochemical environment of the fluorophore that may affect fluorescence lifetime include a change in the local viscosity of the fluorophore, an increase in hydrophobicity of the new environment due to exclusion of previously solvating water and/or a reduction in contact with the aqueous cellular environment, and/or increased protection of the fluorophore from dissolved oxygen. Provided that the fluorophore is in proximity to the binding site, its environment will be altered and its lifetime affected.

The methods of the invention may be used, for example, to detect enzyme activities in living cells by introducing substrates for the enzymes of interest that are labeled with fluorophores and that will bind to endogenous biomolecules in the cell. In certain embodiments, the methods may be used to detect localization of biomolecules that contain the binding domains of interest by introducing synthetically produced versions of the modified products into the cell. In certain embodiments, the methods of the invention may be used in vitro in enzymatic assays by combining the labeled substrate, the enzyme, and a binding biomolecule, which may or may not be the enzyme. The methods of the invention are applicable to any biological modification for which a binding partner exists, which may be found endogenously or introduced exogenously.

The methods of the invention, which allow detection of enzymatic modifications, including real-time rates of modification, can be used as tools for basic research, drug discovery, and in clinical applications. The methods of the invention can be used to detect enzyme activity in vitro in real-time. The in vitro assays may be used, for example, in initial drug discovery processes. Real-time activity detection in high-throughput, e.g., multiwell, format offers the advantage of streamlining many aspects of the process of screening and characterizing potential drug molecules.

As shown in the examples, fluorescence lifetime changes for a Cy5 fluorophore attached to a tyrosine kinase substrate peptide are tyrosine phosphorylation- and kinase activity-dependent. It is hypothesized that the physiochemical basis of the lifetime change is in the binding of the phosphorylated product to a phosphotyrosine-specific domain on the kinase protein (the SH2 domain), and evidence obtained through control experiments support this hypothesis.

Almost all known PTM are recognized by some type of protein binding domain. This recognition, termed orthosteric, is a major factor in governing the downstream transduction of PTM enzymes. Since it is fundamental to the cellular processes for which these PTMs evolved, it is reasonable to infer that all PTMs have the potential to be recognized and bound by some protein. Most, and likely all, PTM binding domains are capable of binding to artificial/unnatural or natural peptide sequences. Most, and likely all, PTM enzymes are capable of modifying synthetic peptides. Accordingly, it is also reasonable to infer that recognition of any PTM-like modification of a biosensor comprising a fluorophore and a polypeptide substrate by (a) binding domain(s) will result in a change in fluorescence lifetime of the fluorophore, most likely an increase in lifetime. Examples of specific PTM/binding domain interactions that illustrate this concept using protein/ligand crystal structures are provided below. In some cases, the modification itself may result in sufficient change in the environment to change the lifetime even in the absence of binding of the modified substrate to a protein. For example, PTM by ubiquitylation may serve to extend the lifetime of a fluorophore bound to the modified substrate. Protein fluorophores such as EGFP-tagged kinase protein may undergo significant conformational changes upon autocatalytic modification or binding to a scaffold, resulting in a change in the lifetime of its fluorophore. Suitable substrates for enabling recognition by both the modifying enzyme and the binding domain may be identified by any suitable method, including array- or screening-based methods that select for both properties. Using available structural information about known protein/polypeptide ligand interactions and screening allows the design and refinement of peptide sequences for use in biosensors in the methods of the invention.

Described in the examples is a cell-penetrating peptide biosensor for dynamic monitoring of phosphorylation by Abl kinase based on FLIM, a method that is not confounded by photobleaching or cellular autofluorescence. In the examples, FLIM was applied to detect phosphorylation-dependent fluorophore lifetime shifts (1-2 ns) in intact, living cells (FIG. 1). It was established that the fluorophore lifetime shift is dependent on phosphorylation specifically by Abl kinase. The fluorophore intensity and lifetime components were mapped to quantify subcellular phosphorylation, and kinase inhibition was monitored in real time. The methods of the invention may be used to interrogate real-time, subcellular signaling activities in cells, particularly cell populations not amenable to expression of genetically engineered biosensor proteins. The methods of the invention may be used to detect other kinases, as well as the enzymes that catalyze other modifications of polypeptide substrates.

FLIM is not affected by photobleaching or intensity and has the potential for single molecule monitoring. Also, time-correlated single photon counting FLIM is capable of highly resolved discrimination between species exhibiting very small differences in lifetimes (even sub-nanosecond), facilitating the mapping of exquisite detail in subcellular images. Described herein is the first demonstration of a FLIM-based phosphorylation biosensor technology that has the potential to circumvent key technological gaps as a new strategy for studying intracellular signaling biology.

Figure 2:
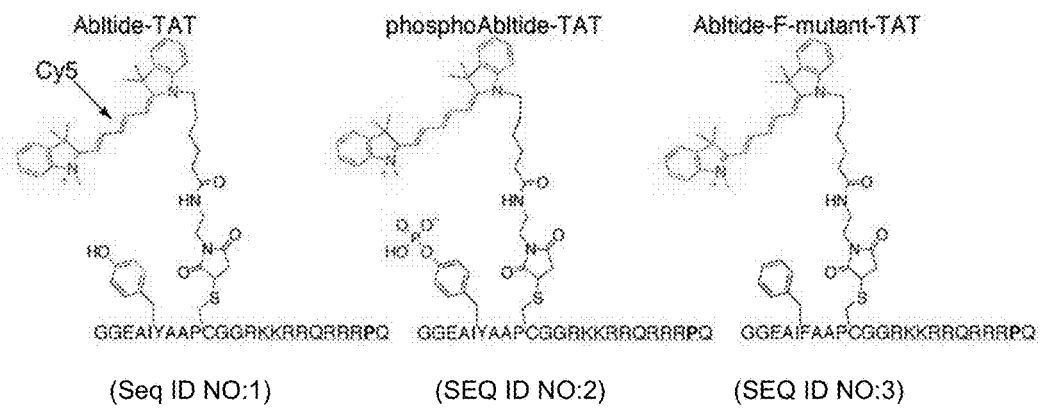
FIG. 2 shows the structures of a peptide-based Abl kinase biosensor including an Abl substrate sequence, a TAT peptide, and a Cy5 label, a phosphorylated positive control, and a Y→F mutated analog.

The methods of the invention employ delivery of organic fluorophore-tagged peptide substrates of enzymes and visualization of enzyme activity in live, intact cells using time-resolved FLIM (FIG. 1). The biosensor used in the examples has the sequence GGEAIYAAPC$_{Cy5}$GGRKKRRQRRRPQ (SEQ ID NO:1) and is designated Abl-TAT, also known as Abltide-TAT (FIG. 2). The Abl-TAT biosensor comprises of an Abl substrate sequence ("Abltide") tagged with a Cy5 fluorophore and a TAT cell penetrating peptide (FIG. 2). Included as controls were a synthetically phosphorylated derivative (known as Abl-phospho or phosphoAbltide-TAT) (FIG. 2, SEQ ID NO:2) of the Abltide-TAT biosensor, and an analog (known as Abl-F mutant or Abltide-F-mutant-TAT) (FIG. 2, SEQ ID NO:3) having a phenylalanine substitution for the tyrosine residue of the Abltide-TAT biosensor. The substrate portion of the biosensor, EAIYAAP (SEQ ID NO:4) is relatively selective for the c-Abl kinase (Abl1) over other tyrosine kinases. However, it is also phosphorylated by the Abl family member Abl2. Abl1 and Abl2 are highly homologous and share many functions in normal cells. As used herein, "Abl kinase" denotes both Abl1 and Abl2. In the examples, FLIM instrumentation with pico second pulsing lasers was used to measure Cy5 lifetime for the unphosphorylated biosensor and a phosphorylated derivative in solution and in live cells.

EXAMPLES

Methods and Materials
Cell Culture.
Control (vector only), FKBP-Abl(NUK) and Abl (−/−) immortalized mouse embryonic fibroblast (MEF) cell lines were a kind gift from Prof. Jean Y. Wang (University of California-San Diego). Cells were maintained in Dulbecco's modified Eagle medium (DMEM) supplemented with 1% penicillin/streptomycin and 10% Fetal Bovine Serum (Atlanta Biologicals, Inc.).
Peptide Synthesis.
Peptides were prepared to >90% purity using Fmoc solid phase peptide synthesis as previously described, and labelled with Cy5-maleimide (Lumiprobe, Inc., Hallendale Beach, Fla., USA).
Peptide Labeling with Cy5-Maleimide.
Peptide (7-10 mg) was dissolved to a final concentration of 1 mM in reaction buffer (2 ml, 6M guanidinium-HCl/100 mM phosphate) containing triscarboxyethylphosphine (TCEP, 1 mM) and adjusted to pH 6.5 with HCl/NaOH as necessary. Cy5-maleimide (1-2 mg, Lumiprobe, Inc., USA) was dissolved in DMSO (20 μl) and added, and the solution vortexed to mix. The reaction was allowed to proceed in the dark at room temperature for 10 h. Reaction progress was checked at 2 h by analyzing an aliquot (1 μl) diluted with water/acetonitrile/trifluoroacetic acid (50/50/0.1%) by MALDI-TOF-MS (linear positive mode) using α-cyano-4-hydroxycinnamic acid as matrix. Labeled peptide was purified by preparative HPLC using a C18 column (Agilent 1200 system with Agilent Zorbax column) and fractions containing predominantly labeled material (as detected by MALDI-TOF MS) were pooled and lyophilized to give 1-2 mg final peptide. Identity and purity were initially confirmed by MALDI-TOF MS. After long-term storage (10 months) in phosphate buffered saline at −20° C., samples were analyzed by LC/MS (ThermoFinnegan Accela-LTQ system) on a C18 column (2.1 I.D.×50 mm L, 1.7 µm particle size, Phenomenex) with a gradient of water/acetonitrile/formic acid (initially 95/5/0.1% rising to 35/65/0.1% at a rate of 6%/min).

FLIM Experiments.

Imaging was performed using scanning confocal time resolved microscopy (Microtime 200 from Picoquant GmbH, Berlin, Germany). A 633 nm 20 MHz picosecond pulse laser source was used for excitation and emission was separated from the excitation beam by a dual band dichroic (z467/638rpc, Chroma) and collected through an apochromatic 60×, 1.2 NA water immersion objective. A 50 µm pinhole was used to reject off-focus photons from the excitation volume, and the overall fluorescence was collected and separated accordingly using a dichroic beam splitter (600 cxr, AHF, Chroma) and filtered by emission filters (670±10 nm) before being detected by two single photon avalanche photodiodes (SPAD) (SPCM-AQR, PerkinElmer Inc.). Fluorescence was measured using the time-correlated single photon counting (TCSPC) time-tagged time-resolved (TTTR) mode (Time Harp200, PicoQuant). Fluorescence lifetime was calculated by fitting TCSPC histograms for each pixel (150×150 pixels total) with a multiexponential model until no pattern of residual is observed. The 150×150 pixel lifetime images were then converted into a matrix form and exported to MATLAB R2011b. The data in the matrices were separated and classified into lifetime and intensity images for visualization and analysis. Notably, images with higher lifetime but lower intensity thresholds are not easily interpreted using conventional FLIM data, thus this extraction process enables quantitative analysis.

After this conversion, the intensity components for each experiment were compared to those of a baseline control (autofluorescence from the cells) to remove background. Autofluorescence for 3T3 cells ranged from 50-100 intensity counts and this value was used as a threshold to remove components from the lifetime image with intensity counts under 80 to minimize contribution to the signal from autofluorescence. After this background removal the 2D images were reconstructed using MATLAB and Image J v. 1.42. Regions of interest (ROIs) comprising an area equivalent to 5×5 to 10×10 pixels were chosen for the same general subcellular compartment for different cells. At least 20 (20-80) different fitted points in each cell from at least 3 cells per view were used, and the data were combined for 3-5 replicate experiments to construct the fitted data comparison.

Figure 3:
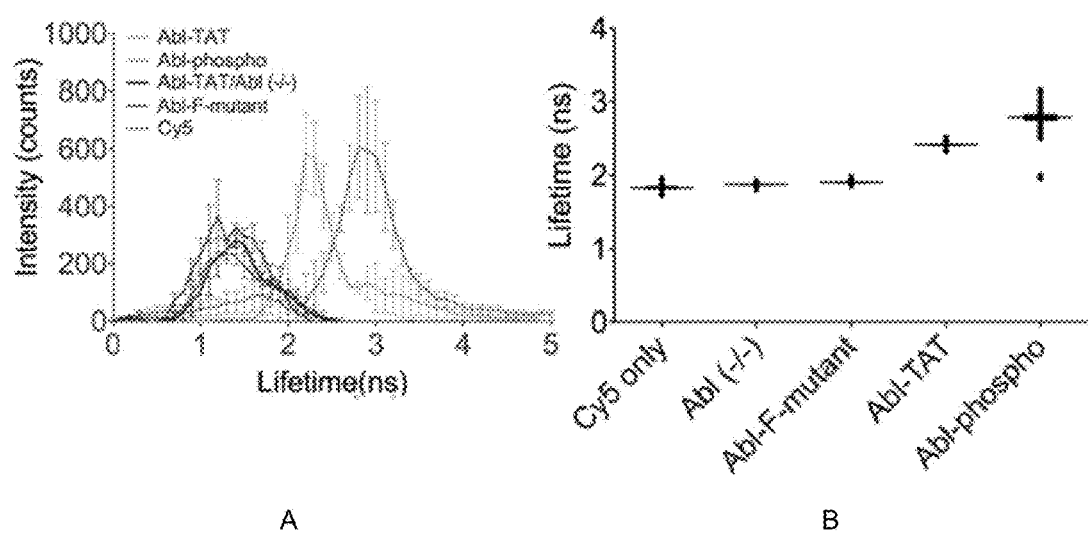
FIG. 3A is a plot of intensity v. lifetime of variously treated cells.
FIG. 3B is a scatter plot of lifetimes in selected regions of interest in similar subcellular locations for cells represented in FIG. 3A.

With reference to FIG. 3, WT MEF cells (unless otherwise indicated) were cultured on cover slips and incubated with the biosensor peptide or a control (as indicated, 50 nM for each) for 24 h, then imaged using the FLIM system. Data were extracted from raw FLIM images and represented as lifetime maps of autofluorescence, Cy5 only, Abl-TAT in Abl (−/−) MEFs, Abl-TAT in WT MEFs, Abl-F-mutant, Abl-phospho. With reference to FIG. 3A, fluorophore lifetime per cell was averaged for at least 20 cells in 3-5 replicate experiments and plotted as a distribution of lifetimes observed in each condition. Error bars represent standard error of the mean for each lifetime value. FIG. 3B shows aligned scatter plots of lifetimes for pixels in selected regions of interest (ROIs) within similar subcellular locations for cells represented in FIG. 3A. Error bars represent SEM.

To quantitatively address the distribution and level of biosensor phosphorylation in different subcellular regions, the intensity and lifetime components of the signal arising from the FLIM measurements were separated and lifetime values plotted in 2D using MatLab. No phosphorylation-dependent intensity increases for this biosensor were observed either in solution or in cells, in contrast to what has been observed by others (Yeh et al. *J Biol Chem* 2002, 277, 11527-11532). The Abl-TAT biosensor was then used to image Abl kinase inhibition with the kinase inhibitor imatinib in control MEFs. MEFs were treated with the biosensor and imaged before (t=0) or after (t=5, 8 min) adding the Abl inhibitor imatinib.

Figure 4:
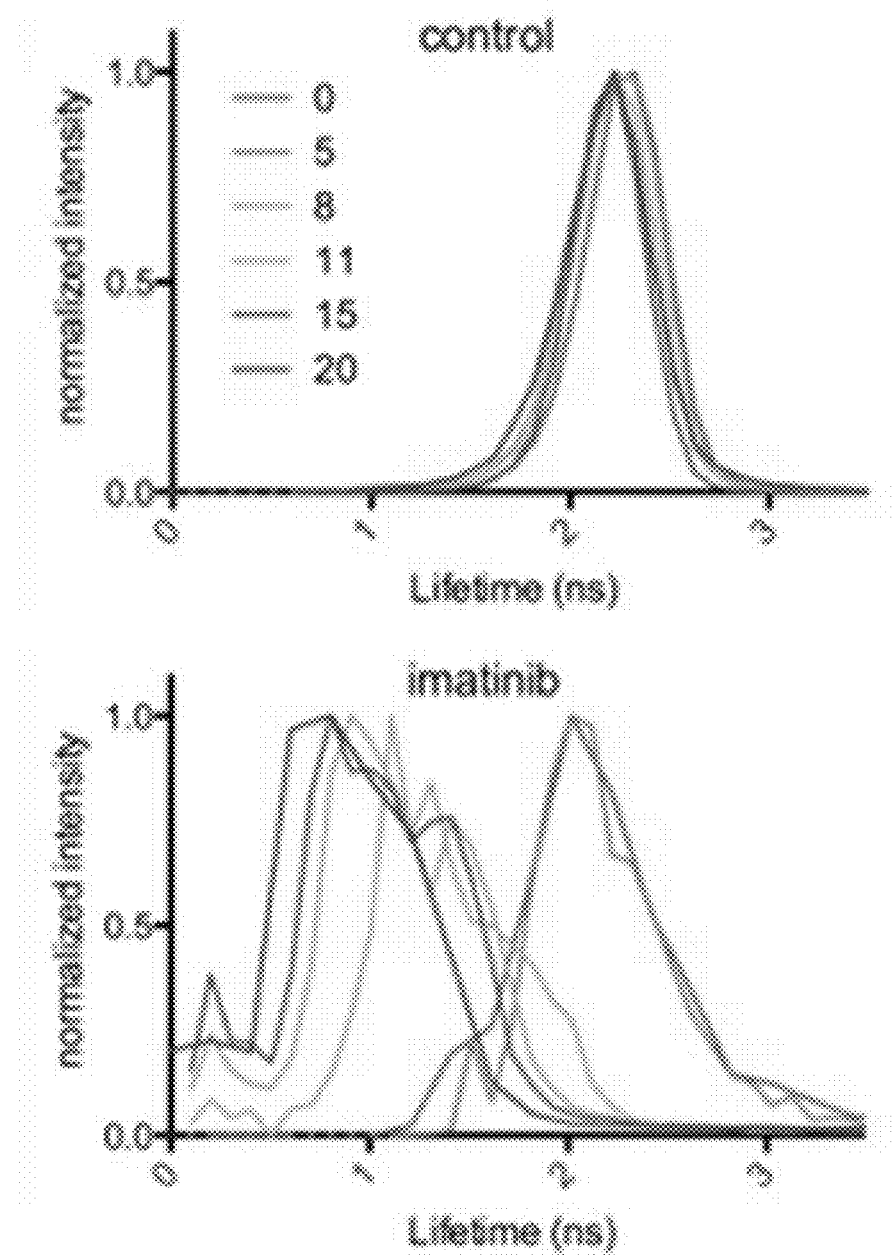
FIG. 4 shows images of subcellular Abl inhibition by imatinib.

With reference to FIG. 4, lifetime distributions for cells treated with the biosensor were plotted at various timepoints (0-20 min) (top panel). MEFs stably expressing a nuclear-enriched Abl kinase mutant, FKBP-Abl(NUK), were also analysed in the presence of imatinib (FIG. 4, lower panel). In the presence of imatinib over the course of 70 min, a general trend towards decreased lifetime overall (e.g. FIG. 4) and negative lifetime shifts in multiple areas of the cell within the first few minutes of incubation were detected, consistent with kinase inhibition and dephosphorylation of the biosensor by phosphatase enzymes. In the absence of imatinib, biosensor lifetime was dynamic but overall no significant decrease in lifetime was observed (FIG. 4, upper panel).

These experiments demonstrate that fluorescence lifetime shifts measured for the cell-deliverable kinase biosensor are phosphorylation-dependent, yielding dynamic information about the localization of kinase (and potentially phosphatase) activity in single living cells. This will make it possible to examine heterogeneous mixtures of cells to dissect subsets of signaling phenotypes and responses to inhibitors. This approach is generalizable to other kinase substrates and fluorophores, enabling analysis of more than one kinase-targeted FLIM biosensor at a time. Currently, other kinase substrate biosensors, e.g. for Syk kinase, are being developed to expand the application of this strategy and achieve simultaneous detection of multiple kinase activities in situ.

This strategy was also found to be effective in detecting activity the tyrosine kinase Syk kinase. Briefly, MCF7 breast cancer cells expressing (Syk +/+) or not expressing (Syk−/−) Syk kinase were co-cultured with cells expressing Syk-EGFP or inactive kinase-EGFP (KD-Syk-EFGP) and incubated with a Cy5-labeled Syk substrate peptide SAStide-TAT (DEEDYEEPDEPGGCCy5GGRKKRRQRRRPQ) (SEQ ID NO:4), and treated with pervanadate, an oxidative stress-inducing compound that activates Syk. The EGFP lifetime was reduced slightly only in cells expressing the active Syk-EGFP, but not in cells expressing the KD-Syk-EGFP), indicating possible energy transfer (FRET) to another fluorophore, in this case Cy5. This FRET is a different photophysical phenomenon than the change in lifetime observed for Cy5 attached to the biosensor, in which the lifetime is extended, rather than shortened, upon phosphorylation and protein binding. The two lifetime shifts (decreased EGFP lifetime and increased Cy5 lifetime) co-localize in active Syk-expressing cells under Syk activation conditions provide evidence of that the biosensor peptide binds to the protein. Further, in Syk +/+ cells that have been pre-treated with the SAStide-TAT-Cy5 biosensor and a Syk inhibitor (fostamatinib, 1 hour), no regions of increased lifetime were observed, supporting the Syk and phosphorylation specificity of the signal.

Biosensor Lifetime Analyses.

For in cell analysis, MEFs were plated on cover slips in 12-well plates at 70% confluency and allowed to recover for 24 h. Wells were washed gently with PBS (3×1 ml) and treated with probe or controls (Abl-TAT, Abl-phospho, Abl-F-mutant, Cy5 alone) (50 nM) in DMEM with FBS for 24 h. Cover slips were washed with PBS and imaged immediately. For imatinib experiments, images were taken before the addition of imatinib to the buffer in which the cover slips were incubated followed by time lapse imaging after addition of imatinib. Control experiments were conducted without imatinib to evaluate the potential for and effect of photobleaching over the experimental time.

In solution, lifetime differences between the phosphorylated and unphosphorylated Abl-TAT peptide species were not significant (data not shown), indicating that phosphorylation alone is not sufficient to elicit a change in the rate of fluorescence signal decay for the Abl-TAT peptide sensor. However, in the presence of c-Abl kinase at 1:1 ratio, robust lifetime differences were observed, and this phenomenon was blocked by pre-incubation of the kinase with higher ratios of unlabelled phosphopeptide. This effect may arise from a change in the local environment of the fluorophore that may occur upon binding of the phosphopeptide with c-Abl kinase, probably through the kinase SH2 domain.

In order to assess the physiochemical basis for the lifetime shift, standards were established in NIH3T3 immortalized mouse embryonic fibroblast cells (MEFs) to assess phosphorylation- and Abl kinase-dependence of the lifetime shifts by using three negative controls, which exhibited lower lifetimes in cells: Cy5 alone, a non-phosphorylatable Y→F peptide sensor analog (Abl-F-mutant) (both in control MEFs expressing Abl kinase), and the Abl-TAT biosensor in Abl(−/−) knockout cells (FIGS. 3B, C and E). Average lifetimes per cell for multiple cells were calculated and plotted to show the distribution of lifetimes observed for the biosensor and each control (FIG. 3G). The distributions were determined to be non-Gaussian, so non-parametric ANOVA with a Dunn's post-test was used to evaluate statistical significance (P<0.05) for differences in the mean lifetimes. There was no significant difference between the Cy5, Abl(−/−) or Abl-F-mutant experiments, however each of these controls exhibited significantly lower mean lifetimes than both Abl-TAT in MEFs expressing Abl kinase and Abl-phospho (positive control). The mean lifetime for Abl-phospho was also significantly longer than that of Abl-TAT, consistent with enrichment of the phosphorylated form of the substrate. These experiments confirmed that the increase in Cy5 lifetime was specific and due to Abl-dependent phosphorylation of the biosensor peptide on tyrosine. As another control to support the interpretation of phosphorylation dependence for lifetime increases in cells, immunocytochemistry was used to show colocalization between the Abl-TAT biosensor and phosphotrosine.

Sequestration of the biosensor in endosomes was tested by staining for an endosomal marker. Minimal, non-exclusive colocalization of the biosensor with endosomes was observed, indicating that the biosensor peptide was not sequestered. Peptide degradation, a potential issue in some cell types, was also examined. Controls using fluorescence correlation spectroscopy (FCS) measured Cy5 alone vs. the Abl-TAT biosensor in MEFs, provided evidence that for MEFs, the signal observed for the Abl-TAT biosensor arose from peptide that was not degraded to free Cy5.

Figure 5:
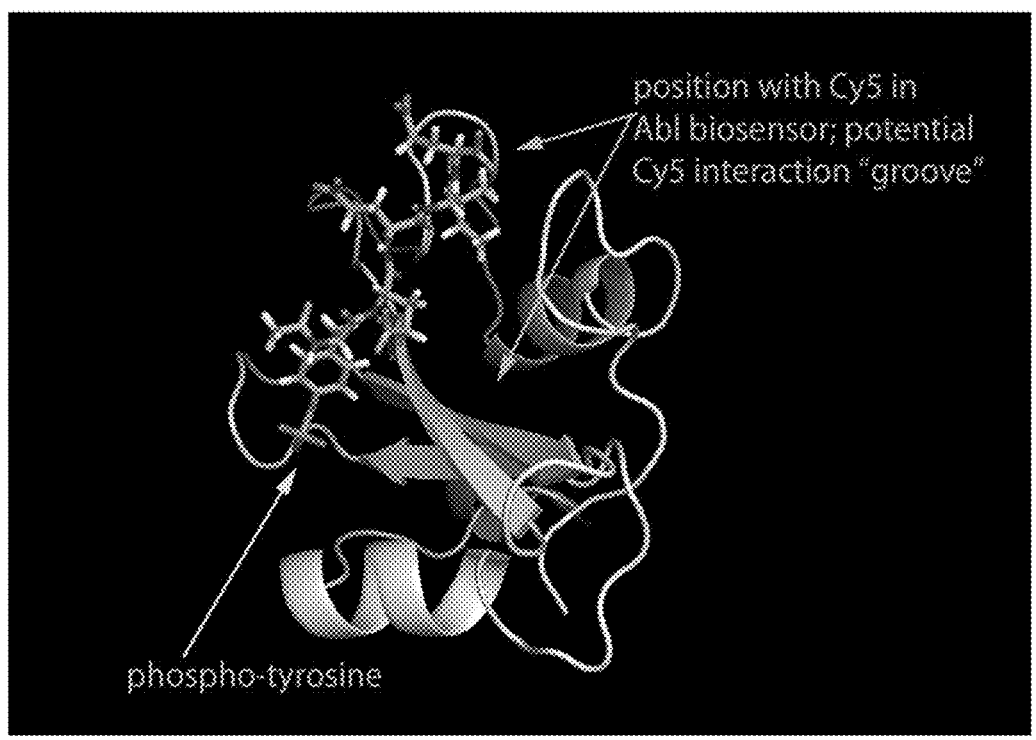
FIG. 5 shows phosphotyrosine recognition and binding.
Figure 6:
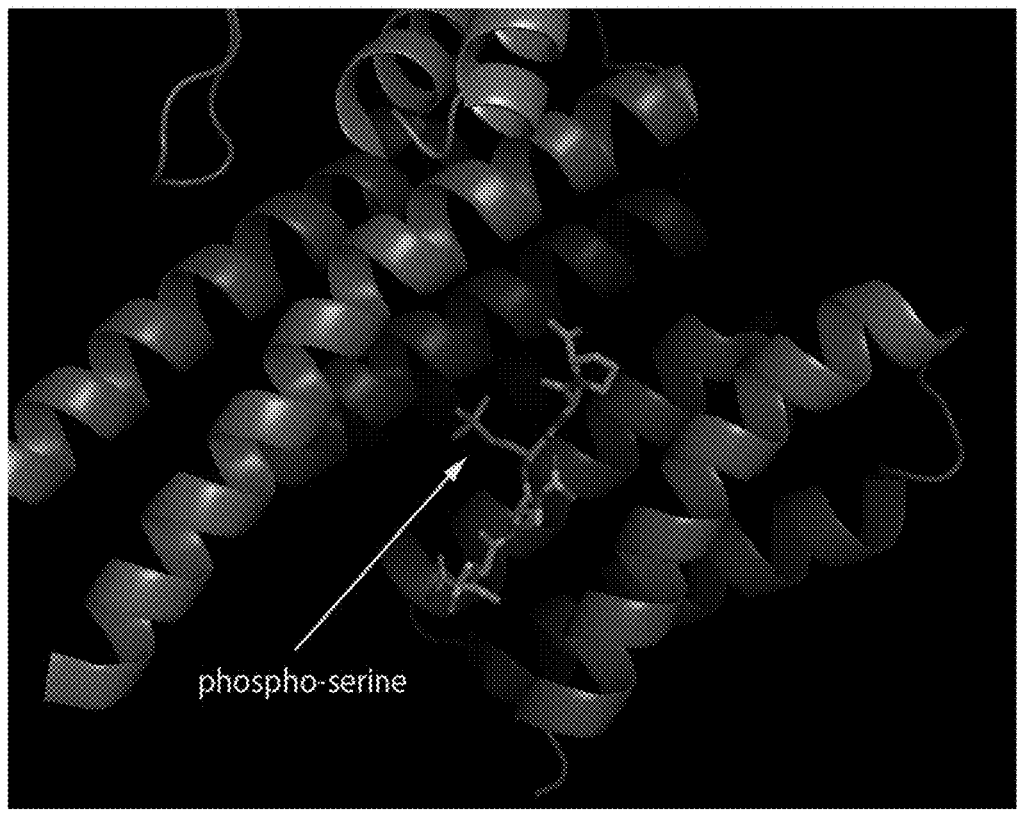
FIG. 6 shows phosphoserine/threonine recognition and binding.
Figure 7:
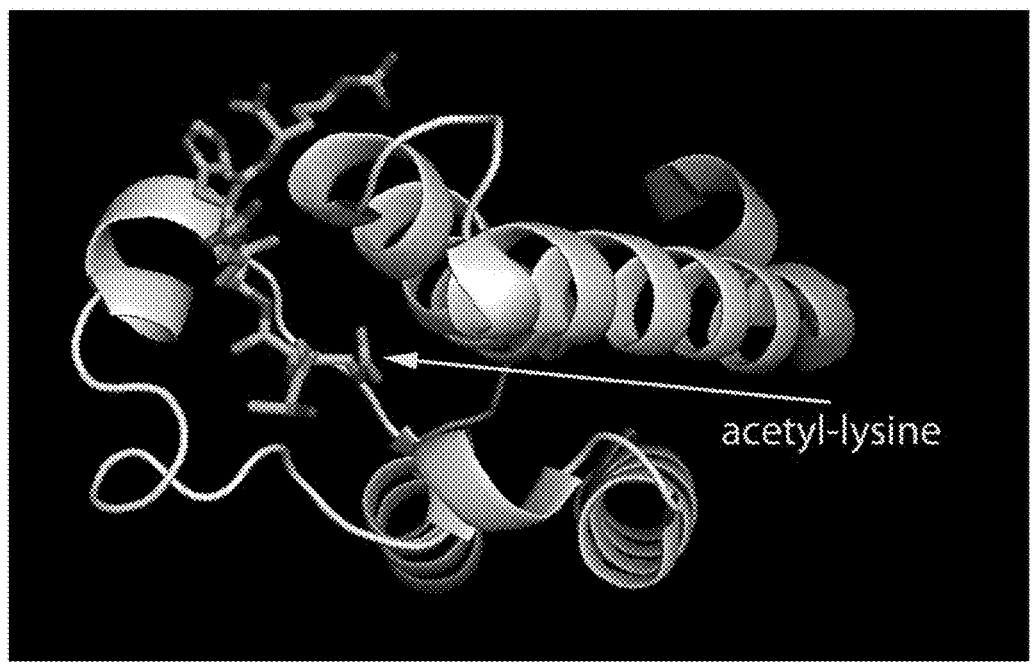
FIG. 7 shows acetylation recognition and binding.
Figure 8:
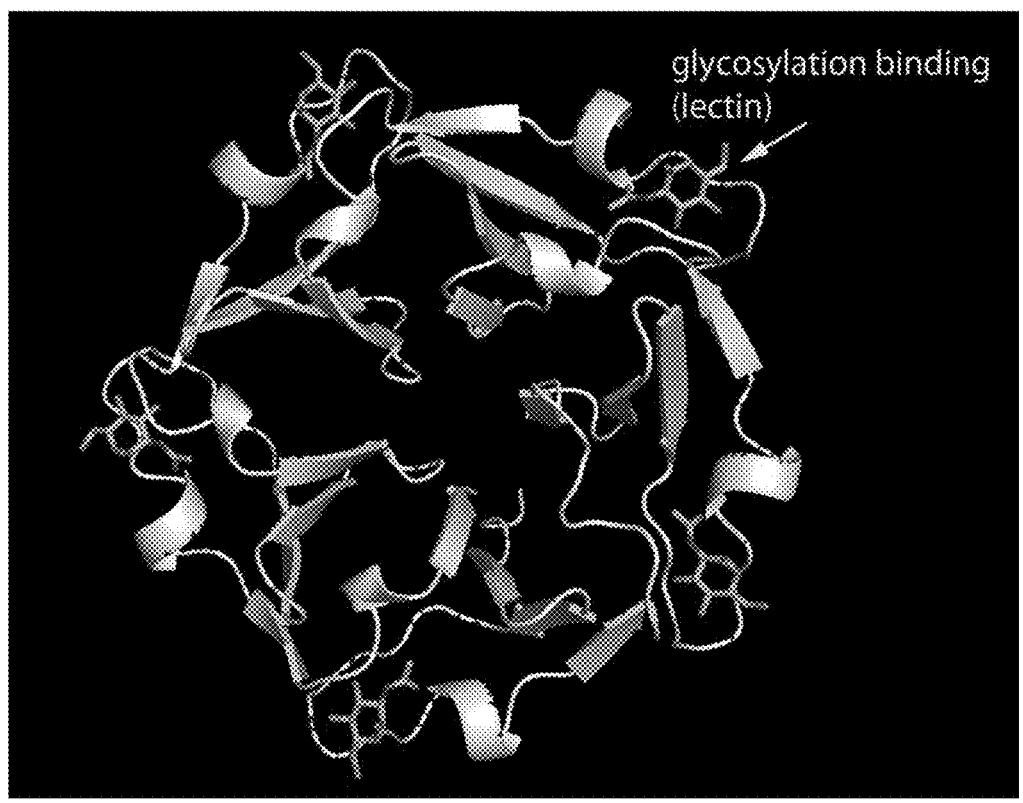
FIG. 8 shows glycolsylation recognition and binding.
Figure 9:
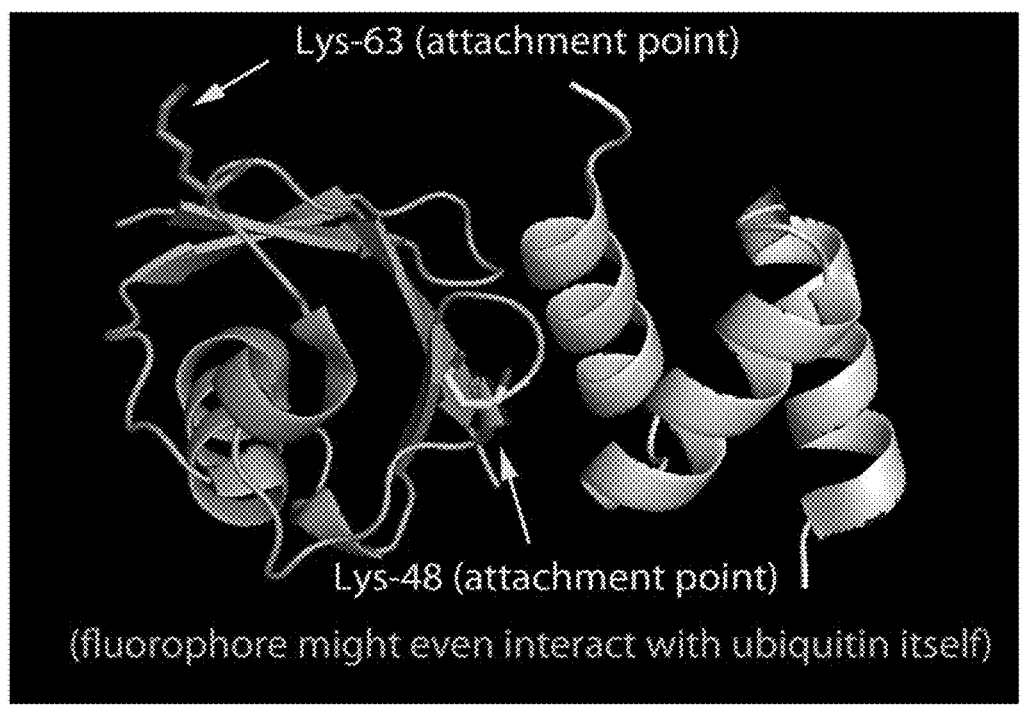
FIG. 9 shows ubiqitylation recognition and binding.
Figure 10:
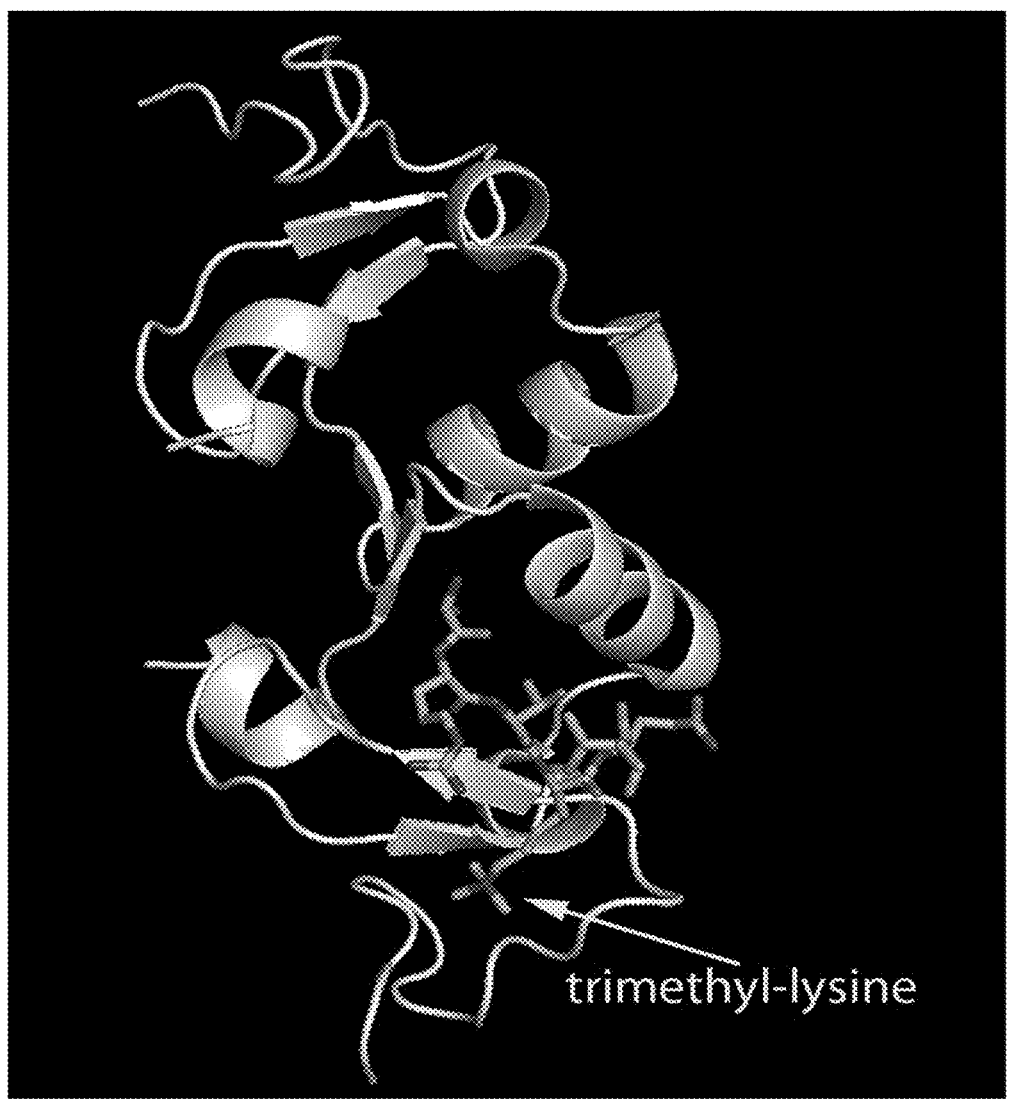
FIG. 10 shows methylation recognition and binding.
Figure 11:
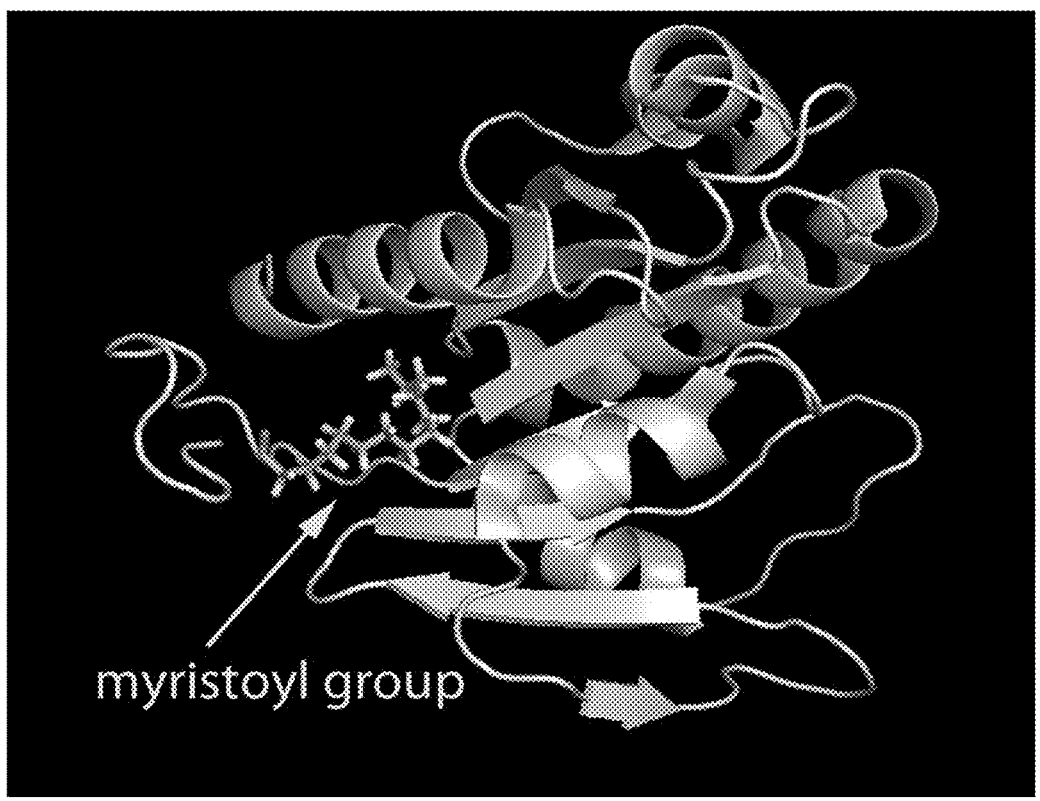
FIG. 11 shows lipidation recognition and binding.
Figure 12:
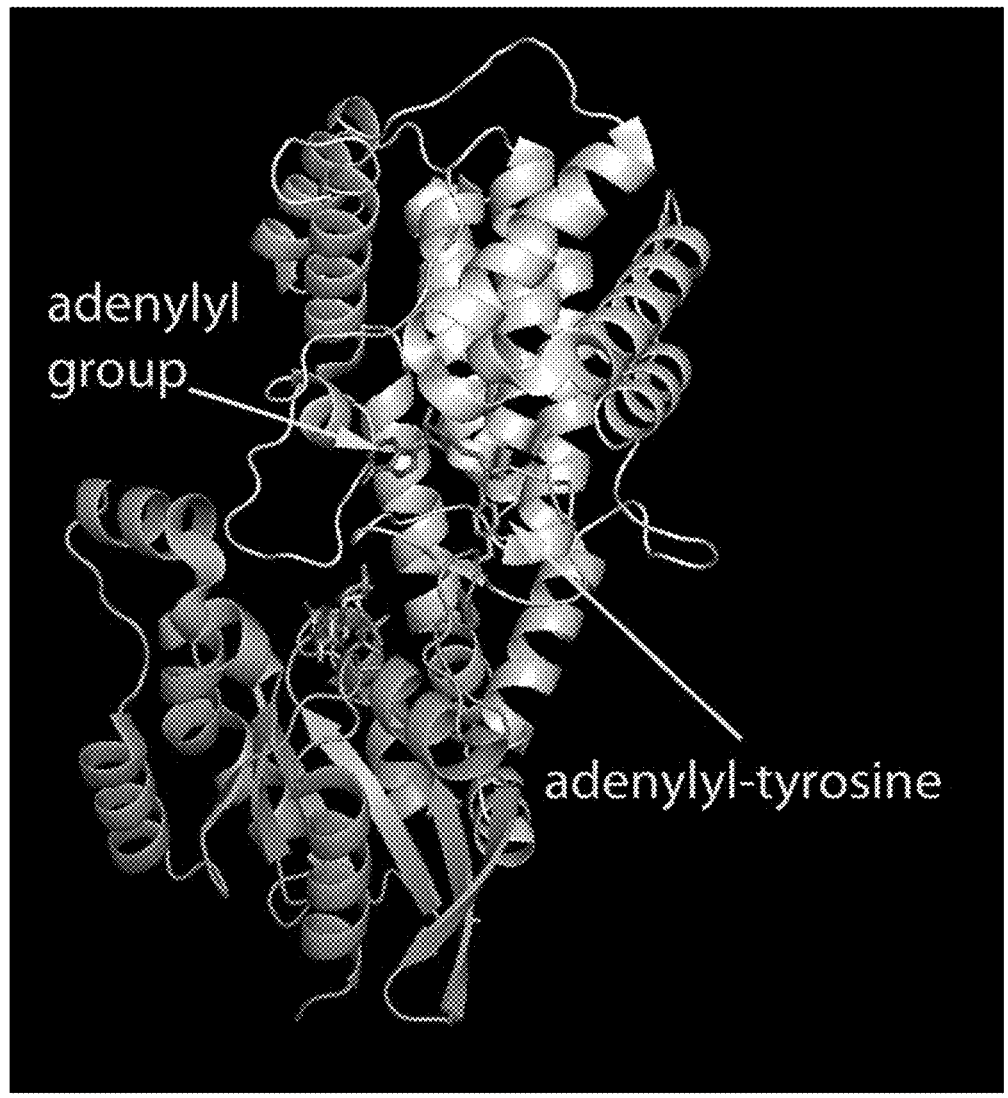
FIG. 12 shows adenylylation recognition and binding.

In order to demonstrate the general applicability of the disclosed methods, figures showing modified substrates in association with its cognate binding protein were generated from published crystal structures of binding complexes retrieved from the Protein Data Bank (PDB) (FIG. 5-11). For each of FIG. 5-12, the molecule containing the modification of interest is shown with the backbone colored in green, while the binding protein is shown as a ribbon cartoon in gray. Modifications are pointed out using yellow arrows. FIG. 5, generated from PDB:1HCT, shows phosphotyrosine recognition and binding. FIG. 6, generated from PDB:2BTP, shows phosphoserine/threonine recognition and binding. FIG. 7, generated from PDB:1E6I, shows acetylation recognition and binding. FIG. 8, generated from PDB:1TL2, shows glycolsylation recognition and binding. FIG. 9, generated from PDB:2JY6, shows ubiqitylation recognition and binding. FIG. 10, generated from PDB:2YYR, shows methylation recognition and binding. FIG. 11, generated from PDB:2K5U, shows lipidation recognition and binding. FIG. 12, generated from PDB:4ITR, shows adenylylation recognition and binding.

It is claimed:

1. A method of detecting phosphorylation activity of an enzyme in a sample, the method comprising:
   contacting the sample with a biosensor, the biosensor comprising a Cy5 fluorophore and a synthetic peptide substrate including the sequence GGEAIYAAPC$_{Cy5}$GGRKKRRQRRRPQ wherein a binding domain between the biosensor and the enzyme consists essentially of the biosensor and the enzyme; and
   monitoring fluorescence lifetime of the fluorophore not in the presence of a quenching moiety to detect phosphorylation of the biosensor.

2. The method of claim 1, wherein the fluorescence lifetime of the fluorophore is monitored by fluorescence lifetime spectroscopy and/or fluorescence lifetime imaging microscopy (FLIM).

3. The method of claim 2, wherein the substrate of the enzyme is a synthetic peptide.

4. The method of claim 2, wherein the substrate of the enzyme is a peptidomimetic.

5. The method of claim 1, wherein the sample comprises an intact cell.

6. The method of claim 5, wherein the biosensor further comprises a cell penetrating peptide.

7. The method of claim 6, wherein the cell penetrating peptide is a TAT peptide.

8. The method of claim 5, wherein the cell is contacted ex vivo.

9. The method of claim 5, wherein the cell is contacted in vivo.

10. The method of claim 5, wherein the cell is contacted by administering the biosensor to an organism comprising the cell.

11. The method of claim 10, wherein the biosensor comprises a targeting moiety for targeting the cell.

12. The method of claim 10, wherein the biosensor is administered to the organism in a suitable vehicle.

13. The method of claim 5, further comprising exposing the cell to a potential inhibitor of the enzyme and assessing the effect of the exposure to the inhibitor on the enzyme activity by the fluorescent lifetime of the fluorophore.

14. The method of claim 1, wherein the sample comprises an enzyme in vitro.

15. The method of claim 1, wherein the step of detection includes detection of phosphorylation of only the biosensor.

* * * * *

SEQUENCE LISTING

```
<160> NUMBER OF SEQ ID NOS: 4

<210> SEQ ID NO 1
<211> LENGTH: 23
<212> TYPE: PRT
<213> ORGANISM: Unknown
<220> FEATURE:
<223> OTHER INFORMATION: synthetic polypeptide
<220> FEATURE:
<221> NAME/KEY: MOD_RES
<222> LOCATION: (10)..(10)
<223> OTHER INFORMATION: Cy5 label

<400> SEQUENCE: 1

Gly Gly Glu Ala Ile Tyr Ala Ala Pro Cys Gly Gly Arg Lys Lys Arg
1               5                   10                  15

Arg Gln Arg Arg Arg Pro Gln
            20

<210> SEQ ID NO 2
```

```
<211> LENGTH: 23
<212> TYPE: PRT
<213> ORGANISM: unknown
<220> FEATURE:
<223> OTHER INFORMATION: synthetic
<220> FEATURE:
<221> NAME/KEY: MOD_RES
<222> LOCATION: (10)..(10)
<223> OTHER INFORMATION: Cy5 label

<400> SEQUENCE: 2

Gly Gly Glu Ala Ile Phe Ala Ala Pro Cys Gly Gly Arg Lys Lys Arg
1               5                   10                  15

Arg Gln Arg Arg Arg Pro Gln
            20

<210> SEQ ID NO 3
<211> LENGTH: 7
<212> TYPE: PRT
<213> ORGANISM: unknown
<220> FEATURE:
<223> OTHER INFORMATION: synthetic

<400> SEQUENCE: 3

Glu Ala Ile Tyr Ala Ala Pro
1               5

<210> SEQ ID NO 4
<211> LENGTH: 27
<212> TYPE: PRT
<213> ORGANISM: unknown
<220> FEATURE:
<223> OTHER INFORMATION: synthetic
<220> FEATURE:
<221> NAME/KEY: MOD_RES
<222> LOCATION: (14)..(14)
<223> OTHER INFORMATION: Cy5 label

<400> SEQUENCE: 4

Asp Glu Glu Asp Tyr Glu Glu Pro Asp Glu Pro Gly Gly Cys Gly Gly
1               5                   10                  15

Arg Lys Lys Arg Arg Gln Arg Arg Arg Pro Gln
            20                  25
```